(12) United States Patent
Kim et al.

(10) Patent No.: US 6,988,991 B2
(45) Date of Patent: Jan. 24, 2006

(54) THREE-DIMENSIONAL ULTRASOUND IMAGING METHOD AND APPARATUS USING LATERAL DISTANCE CORRELATION FUNCTION

(75) Inventors: Nam Chul Kim, Daegu (KR); Hyun Joo So, Daegu (KR); Sang Hyun Kim, Busan (KR); Jun Ho Lee, Daegu (KR)

(73) Assignee: Medison Co., Ltd., Hongchun-gun (KR)

( * ) Notice: Subject to any disclaimer, the term of this patent is extended or adjusted under 35 U.S.C. 154(b) by 230 days.

(21) Appl. No.: 10/434,173

(22) Filed: May 9, 2003

(65) Prior Publication Data

US 2004/0006273 A1    Jan. 8, 2004

(30) Foreign Application Priority Data

May 11, 2002    (KR) ...................... 10-2002-0026010

(51) Int. Cl.
  *A61B 8/00*    (2006.01)
(52) U.S. Cl. ........................................ 600/443; 128/916
(58) Field of Classification Search ........ 600/443–447; 128/916
  See application file for complete search history.

(56) References Cited

U.S. PATENT DOCUMENTS

| | | | |
|---|---|---|---|
| 5,477,272 A * | 12/1995 | Zhang et al. ........... | 375/240.06 |
| 5,582,173 A | 12/1996 | Li | |
| 5,822,007 A * | 10/1998 | Knee et al. .............. | 348/416.1 |
| 5,876,342 A * | 3/1999 | Chen et al. .................. | 600/443 |
| 6,059,727 A * | 5/2000 | Fowlkes et al. ............. | 600/443 |
| 6,106,470 A * | 8/2000 | Geiser et al. ................ | 600/443 |
| 6,755,787 B2 * | 6/2004 | Hossack et al. ............ | 600/447 |

OTHER PUBLICATIONS

D. F. Leotta, et al., IEEE Proc. Ultrasonics Symposium '95, vol. 2, pp. 1415-1418, "Three-Dimensionl Ultrasound Imaging Using Multiple Magnetic Tracking Systems and Miniature Magnetic Sensors", Nov. 1995.

N. Pagoulatos, et al., IEEE Transactions on Information Technology in Biomedicine, vol. 3, No. 4, pp. 278-288, "Interactive 3-D Registration of Ultrasound and Magnetic Resonance Images Based on a Magnetic Position Sensor", Dec. 1999.

(Continued)

*Primary Examiner*—Francis J. Jaworski
(74) *Attorney, Agent, or Firm*—Oblon, Spivak, McClelland, Maier & Neustadt, P.C.

(57) ABSTRACT

Disclosed is a three-dimensional ultrasound image method and apparatus for reducing distortions of ultrasound images by precisely estimating a distance between consecutive two-dimensional frames obtained by a manual scanning. The apparatus comprises a transducer array for transmitting ultrasound signals to a target object and receiving echo signals reflected from the target object; a receive-focusing unit for receive-focusing the echo signals to generate a plurality of consecutive two-dimensional ultrasound image frames; a converter for converting the consecutive two-dimensional ultrasound image frames into a three-dimensional ultrasound image; and a display for displaying the three-dimensional ultrasound image. The method comprises the steps of, a) transmitting and receiving ultrasound signals; b) receive-focusing echo signals to generate a plurality of consecutive two-dimensional ultrasound image frames; c) converting the consecutive two-dimensional ultrasound image frames into a three-dimensional ultrasound image; and d) displaying the three-dimensional ultrasound image.

9 Claims, 9 Drawing Sheets

OTHER PUBLICATIONS

T. White, et al., IEEE Proc. 18th Annual International Conference of the IEEE Engineering in Medicine and Biology Society, vol. 5, pp. 2109-2110, "A Real-Time 3D Ultrasonic Imager Based on a 128×128 Transducer Array", Jan. 1996.

J.-M. Bureau, et al., IEEE Proc. Ultrasonics Symposium '98, vol. 2, pp. 1065-1068, A Two-Dimensional Transducer Array for Real-Time 3D Medical Ultrasound Imaging:, Feb. 1998.

* cited by examiner $$b = \frac{A+B}{2}, \quad c = \frac{A+C}{2}, \quad d = \frac{A+B+C+D}{4}$$

Fig. 9
Before linear interpolation
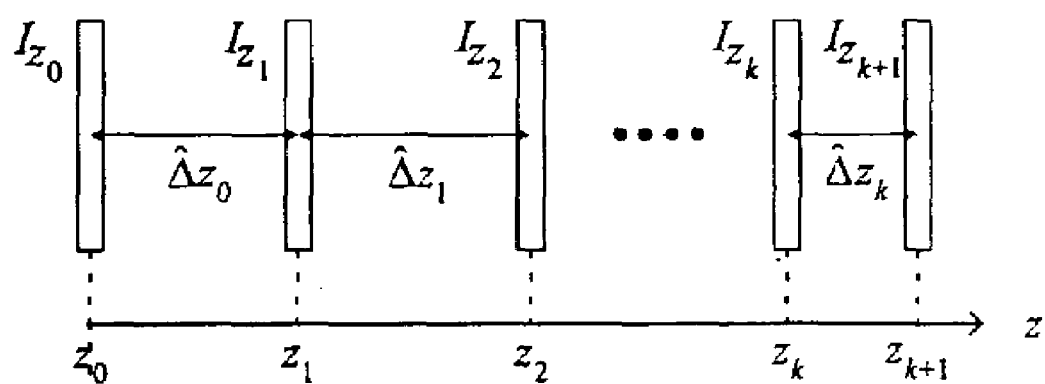
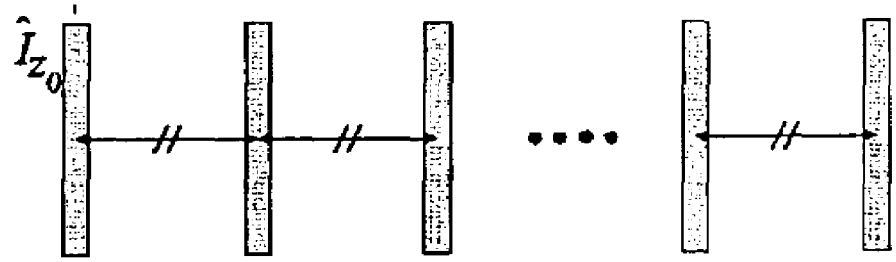
After linear interpolation

THREE-DIMENSIONAL ULTRASOUND IMAGING METHOD AND APPARATUS USING LATERAL DISTANCE CORRELATION FUNCTION

FIELD OF THE INVENTION

The present invention relates generally to ultrasound imaging, and more particularly, to a three-dimensional ultrasound imaging method and apparatus for reducing distortions in ultrasound images, which constructs three-dimensional ultrasound images by precisely estimating the distance between consecutive two-dimensional frames obtained by manual scanning using a lateral distance correlation function.

BACKGROUND OF THE INVENTION

Conventionally, three-dimensional ultrasound images are obtained by rendering a three-dimensional volume consisting of consecutive two-dimensional frames stacked one-by-one. However, where the distance between stacked consecutive two-dimensional frames is not uniform, the three-dimensional ultrasound images constructed from the two-dimensional frames may be distorted. For example, if a target object is an organ in a human body, then the constructed three-dimensional organ may appear distorted from its actual shape due to the non-uniformity of the distance between consecutive two-dimensional frames that represent the organ.

Such non-uniformity typically results from the variation of the movement speed of the probe. Where a probe scans a target object within a certain diagnostic region, the number of consecutive two-dimensional frames obtained is inversely proportional to the movement speed of the probe in that region. For example, if the probe scans a target object within a diagnostic region at a high movement speed, the number of consecutive two-dimensional frames obtained is less than the probe scans at a low movement speed. Thus, relative to the actual target object, a three-dimensional image of a target object may be contracted in size, if it is constructed from consecutive two-dimensional frames obtained at a high movement speed or enlarged in size, if constructed from consecutive two-dimensional frames obtained at a low movement speed. As the variation of the movement speed of the probe increases, the non-uniformity worsens.

In order to compensate for the non-uniformity, a conventional three-dimensional ultrasound imaging system employs both mechanical and non-mechanical means.

The mechanical means comprises: mechanical scanning without using the operator's hands; free-hand scanning using a probe with a location detection sensor (see D. F. Leotta, P. R. Detmer, O. H. Gilja, and J. M. Jong, "Three-dimensional ultrasound imaging using multiple magnetic tracking systems and miniature magnetic sensors," IEEE Proc. Ultrasonics Symposium '95, vol. 2, pp. 1415, November 1995 and N. Pagoulatos, W. S. Edwards, D. R. Haynor, and Y. Kim, "Interactive 3D registration of ultrasound and magnetic resonance images based on a magnetic position sensor," IEEE Trans. Inform. Technol. Biomedicine, vol. 34, pp. 278–288, December 1999); and scanning with a three-dimensional probe (see T. White, K. Erikson, and A. Nicoli, "A real-time 3D ultrasonic imager based on a 128/spl times/128 transducer array," IEEE Proc. 18th Annual International Conference of Engineering in Medicine and Biology Society, vol. 5, pp. 2109–2110, January 1997 and J. M. Bureau, W. Steichen, and G. Lebail, "A two-dimensional transducer array for real-time 3D medical ultrasound imaging," IEEE Proc. Ultrasonics Symposium '98, vol. 2, pp. 1065–1068, February 1998).

The non-mechanical means comprises a stationary correlation function to estimate the distance between consecutive two-dimensional frames obtained by driving a probe, with respect to an elevation distance of a probe obtained from consecutive reference frames, i.e., a distance between that frames, without using a location detection sensor as in manual scanning means (see M. Li, "System and method for 3-D medical imaging using 2-D scan data," U.S. Pat. No. 5,582,173, 1996). As is well known in the art, the stationary correlation function means a function that is invariant to the calculated position. This non-mechanical means calculates a reference elevation distance correlation function ρ(d) based on reference frames, which are obtained from a tissue that is similar to a target object, to estimate the distance between consecutive frames.

According to this non-mechanical means, each of the input frames is classified into a plurality of blocks and an elevation distance correlation $\rho_z^n$ for each block is calculated. A mean elevation distance correlation for each input frame is estimated by averaging all of the elevation distance correlations $\rho_z^n$ with weights and the distance between the input frames is estimated by applying the mean elevation distance correlation to the reference elevation distance correlation function ρ(d). The elevation distance correlation $\rho_z^n$ of each block is defined by:

$$\rho_z^n = \frac{\sum_{(x,y)\in B_n} [I_z(x,y) - \bar{I}_z^n][I_{z+\Delta z}(x,y) \bar{I}_{z+\Delta z}^n]}{\sqrt{\sum_{(x,y)\in B_n} [I_z(x,y) - \bar{I}_z^n]^2 \sum_{(x,y)\in B_n} [I_{z+\Delta z}(x,y) - \bar{I}_{z+\Delta z}^n]^2}} \quad \text{(Eq. 1)}$$

wherein $I_z(x,y)$ is a brightness value corresponding to coordinates (x, y, z) in a three-dimensional space; $B_n$ is an $n^{th}$ block of a frame; $\bar{I}_z^n$ is an average brightness value within a block; and Δz is a distance from a frame located at a position z to a consecutive frame. $\rho_z$ is an elevation distance correlation between frames and is obtained from the elevation distance correlation $\rho_z^n$ of each block. By applying $\rho_z$ to an equation $\Delta z = \rho^{-1}(\rho_z)$, a distance Δz between consecutive two-dimensional frames may be estimated. The equation $\Delta z = \rho^{-1}(\rho_z)$ utilizes an inverse function of the reference elevation distance correlation function ρ(d).

However, the aforementioned means have disadvantages. With the mechanical means, the distance between frames may be accurately obtained. However, since probes must be mechanically fixed or provided with additional devices, patients and operators feel uncomfortable. Further, the associated manufacturing costs of ultrasound imaging apparatuses are increased. In particular, using a three-dimensional probe requires more ultrasound sensor arrays than a two-dimensional probe, and thereby increases the manufacturing cost of the ultrasound imaging apparatus and the size of probe. If the size of probe is increased, an operator may not easily handle the probe when diagnosing a patient.

The non-mechanical means may be more comfortable for operators and patients, and does not require additional sensors or devices. However, since the non-mechanical means employs a fixed elevation distance correlation function, without taking into account the non-stationary characteristics of ultrasound images, obtaining an accurate distance between consecutive two-dimensional frames is very difficult and results in lower reliability of the measured ultrasound images.

Thus, need exists for a method for accurately estimating the distance between frames from images obtained through manual scanning without using mechanical devices or location detection sensors.

SUMMARY OF THE INVENTION

Therefore, an objective of the present invention is to provide a three-dimensional ultrasound imaging method and apparatus for reducing image distortions on three-dimensional ultrasound imaging by accurately estimating a distance between consecutive two-dimensional frames that are obtained through a manual scanning by means of a lateral distance correlation function.

In accordance with the present invention, a three-dimensional ultrasound imaging apparatus is provided, comprising: a transducer array for transmitting ultrasound signals to a target object and receiving echo signals reflected from the target object, wherein the transducer array is comprised of a plurality of transducer elements; means for receive-focusing the echo signals from the transducer array to generate a plurality of consecutive two-dimensional ultrasound image frames; means for converting the consecutive two-dimensional ultrasound image frames into a three-dimensional ultrasound image by aligning the consecutive two-dimensional ultrasound image frames with no offset to each other in a three-dimensional space and interpolating a distance between two adjacent frames among the consecutive two-dimensional frames, to thereby make an inter-frame distance uniform; and a display for displaying the three-dimensional ultrasound image.

Also, in accordance with the present invention, a three-dimensional ultrasound imaging method is provided, comprising the steps of: a) transmitting ultrasound signals to a target object and receiving echo signals reflected from the target object; b) receive-focusing the echo signals to generate a plurality of consecutive two-dimensional ultrasound image frames; c) converting the consecutive two-dimensional ultrasound image frames into a three-dimensional ultrasound image by aligning the consecutive two-dimensional ultrasound image frames with no offset to each other in a three-dimensional space and interpolating a distance between two adjacent frames among the consecutive two-dimensional frames, to thereby make an inter-frame distance uniform; and d) displaying the three-dimensional ultrasound image.

BRIEF DESCRIPTION OF THE DRAWINGS

The features of the present invention, which are believed to be novel, are set forth with particularity in the appended claims. The present invention, both as to its organization and manner of operation, together with further objects and advantages thereof, may best be understood with reference to the following description, taken in conjunction with the accompanying drawings.

FIG. 9 illustrates the uniform inter-frame distance resulting from the linear interpolation with respect to two-dimensional consecutive frames.

DETAILED DESCRIPTION OF THE PRESENT INVENTION

Figure 1:
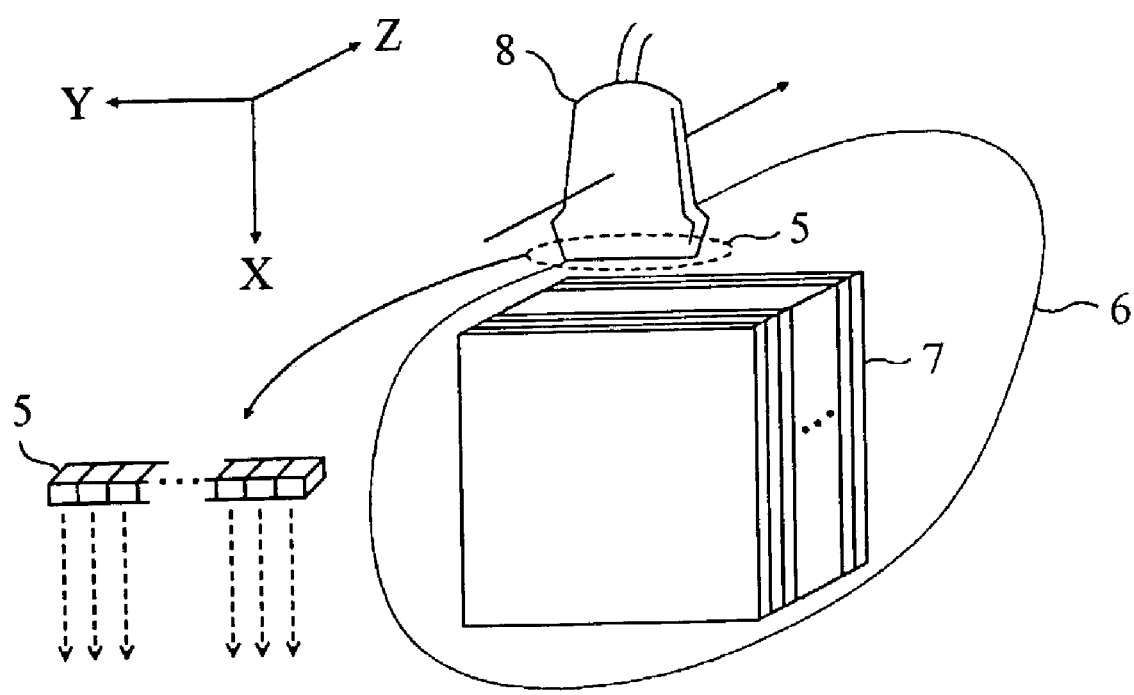
FIG. 1 illustrates obtaining a plurality of two-dimensional (2D) consecutive frames using a probe in a three-dimensional (3D) space.

Referring to FIG. 1, which illustrates obtaining a plurality of consecutive two-dimensional (2D) frames by using a probe in a three-dimensional (3D) space. 3D space is expressed in terms of an orthogonal coordinate system of depth-lateral-elevation (X-Y-Z). Assuming that transducer array 5 is arranged in a lateral direction along the Y-axis, all frames 7 for target object 6 are located in the X-Y plane, and the interface of 2D probe 8 with target object 6 is always perpendicular to the X-axis. However, where a plurality of frame sequences are obtained by using 2D probe 8, 2D probe 8 moves non-linearly according to the shape of the curved surface of target object 6 so that the 3D positions of frames 7 are offset.

Figure 2:
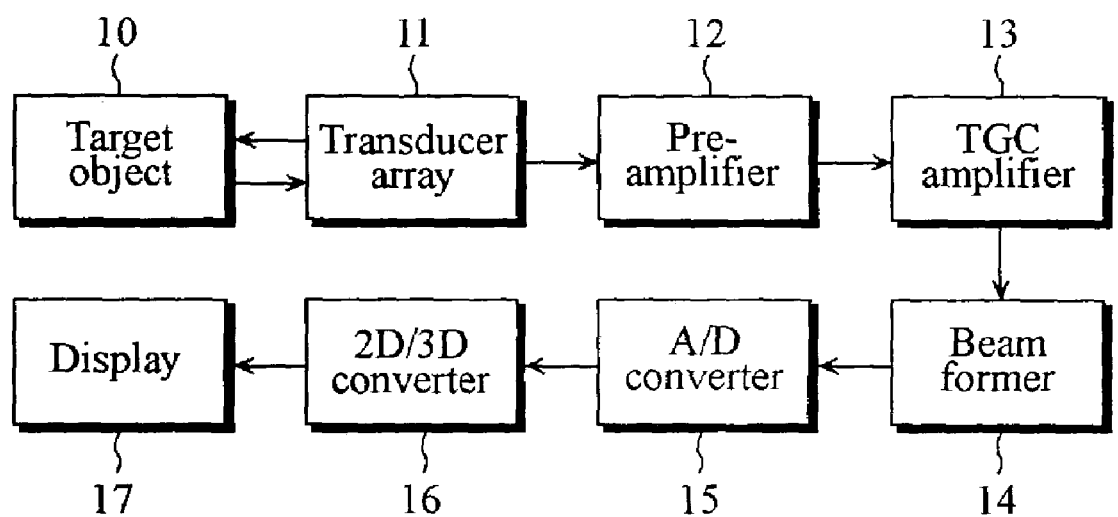
FIG. 2 is a block diagram of a 3D ultrasound imaging apparatus according to the present invention.

Referring to FIG. 2, which shows a block diagram of a 3D ultrasound imaging apparatus according to the present invention. Transducer array 11 transmits ultrasound signals to target object 10 and receives echo signals reflected from target object 10. The echo signals received by transducer array 11 are amplified to a predetermined level by pre-amplifier 12. Time gain compensation (TGC) amplifier 13 amplifies the signals from pre-amplifier 12 by varying a gain with respect to time in order to compensate for attenuation of the ultrasound signals within a human body.

Beamformer 14 receives the amplified signals from TGC amplifier 13 with different delays. Beamformer 14 then sums the delayed signals to receive-focus them on a reflection point of target object 10 in the lateral direction by varying the amount of the delay. Analog-to-digital (A/D) converter 15 converts the signals processed in beamformer 14 from analog to digital. 2D/3D converter 16 receives the digital signals outputted from A/D converter 15 and constructs 3D ultrasound images from 2D ultrasound image frames. The 3D ultrasound images outputted from 2D/3D converter 16 are displayed on display 17.

Figure 3:
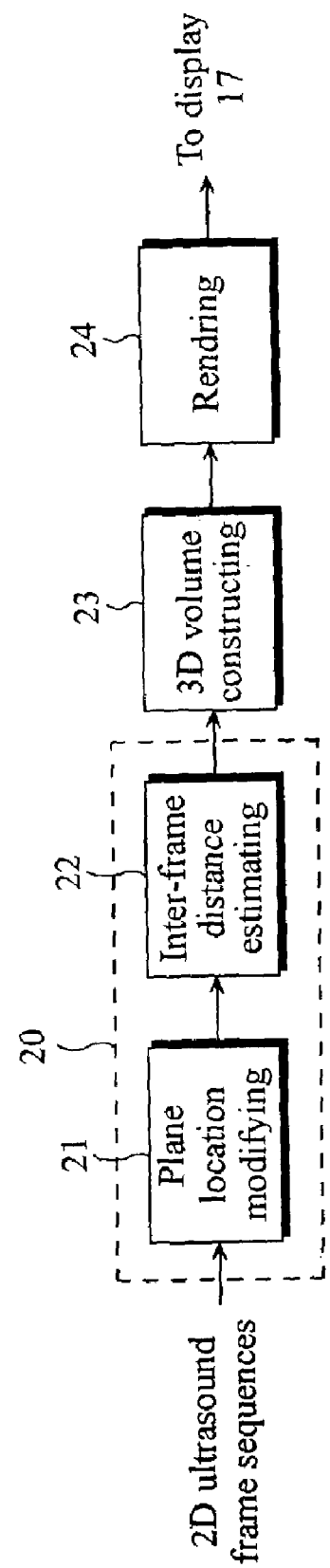
FIG. 3 is a detailed block diagram of the 2D/3D converter shown in FIG. 2.

Referring to FIG. 3, which shows a block diagram of 2D/3D converter 16 shown in FIG. 2. 2D/3D converter 16 comprises pre-processing unit 20, 3D volume constructing unit 23, and rendering unit 24. Pre-processing unit 20 is comprised of plane location modifying unit 21 and inter-frame distance estimating unit 22. Plane location modifying unit 21 aligns frames in a three-dimensional manner by estimating movement of two adjacent frames in the upper, lower, right, and left directions with respect to a plane location in 3D space. Inter-frame distance estimating unit 22 estimates a distance between the two aligned frames and interpolates them to have a uniform inter-frame distance. 3D volume constructing unit 23 obtains 3D volume information from the uniform aligned 2D frames. Rendering unit 24 constructs 3D images through a rendering process on the basis of the 3D volume information.

Figure 4:
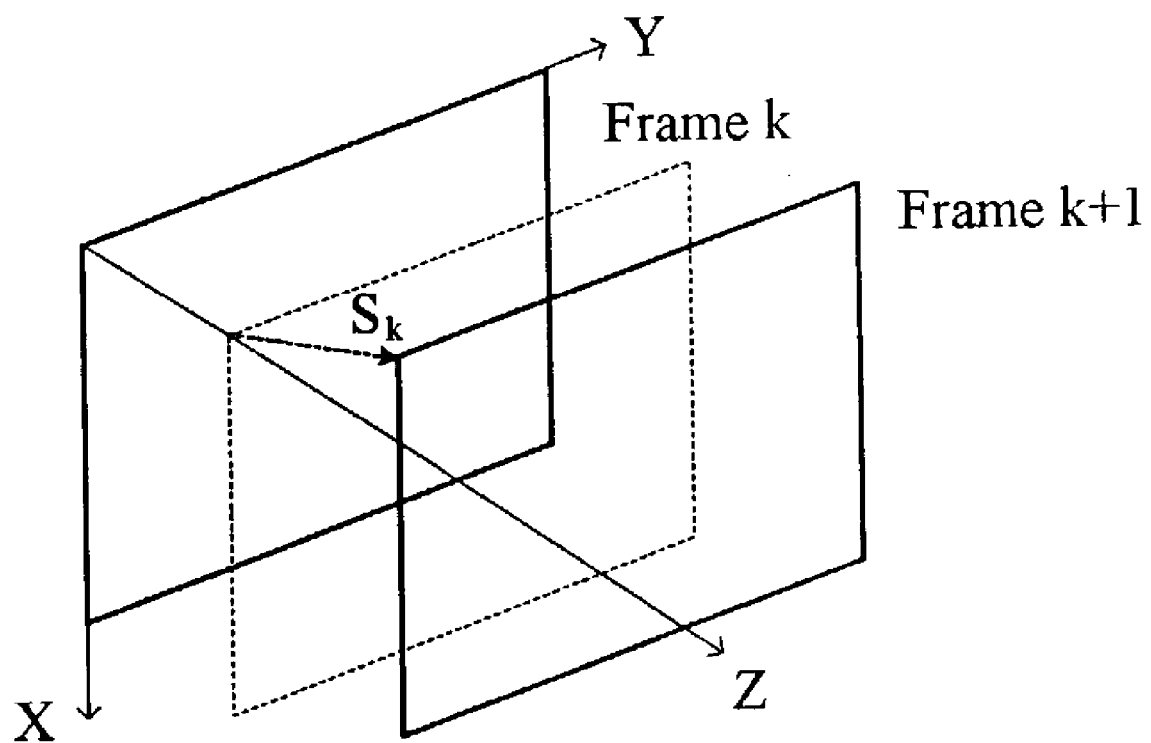
FIG. 4 illustrates the view of an offset of two frames in a 3D space.

Plane location modifying unit 21 estimates movement between frames in the upper, lower, right, and left directions and modifies the estimated movement to align the frames in a 3D space. Referring to FIG. 4, which illustrates the offset of two frames in 3D space. Predetermined coordinates ($x_k$, $y_k$) of a $k^{th}$ frame are located at coordinates ($x+x_k$, $y+y_k$, $z_k$) in 3D space. The coordinates ($x_k$, $y_k$) denote a vector representing how far the $k^{th}$ frame is from a starting point in the 3D coordinates system. Vector ($x_{k+1}$, $y_{k+1}$) representing the location of the next $(k+1)^{th}$ frame is obtained by summing the coordinates ($x_k$, $y_k$) and a vector $s_k=(\Delta x_k, \Delta y_k)$ representing the movement between frames. As can be seen from FIG. 4, the $k^{th}$ and $(k+1)^{th}$ frames are offset in 3D space. That is, the $(k+1)^{th}$ frame moves toward the lower-right direction in 3D space with respect to the $k_{th}$ frame so that their locations in the X-Y plane are different from each other. If the offset between the two frames is not considered while image reconstruction is performed directly through 3D volume constructing unit 23 and rendering unit 24, a reconstructed 3D image may be distorted.

Figure 5:
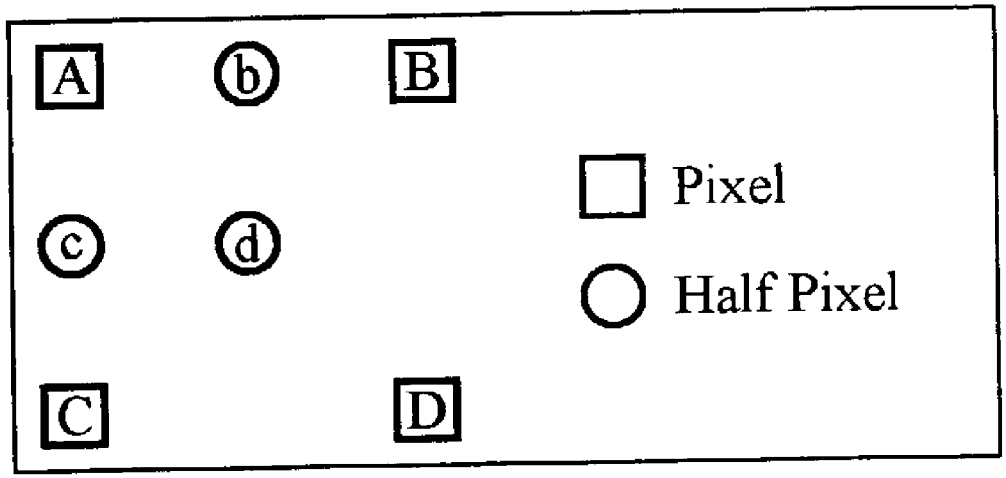
FIG. 5 illustrates bilinear interpolation.

In order to align the plurality of frames with no offset in the 3D space, plane location modifying unit 21 estimates a movement vector by using a block matching algorithm (BMA). For the purpose of estimation, plane location modifying unit 21 divides each of the frames into a plurality of blocks, none of which overlap each other, and matches the blocks up to a half pixel by using a bilinear interpolation method, as shown in FIG. 5, to thereby obtain the movement vector per each block. In FIG. 5, pixels A, B, C, D are represented by the symbol "□" and half pixels b, c, d are represented by the symbol "○." Locations of half pixels between pixels A, B, C, D maybe expressed as $$b = \frac{A+B}{2}, c = \frac{A+C}{2}, d = \frac{A+B+C+D}{4}.$$

Accordingly, matching the blocks of each of the frames up to the half pixels may improve the accuracy of 3D ultrasound images to be displayed on display 17.

Plane location modifying unit 21 obtains a movement vector per each block and determines vector $S_k$ having the highest frequency among the obtained movement vectors to computes a movement vector for each of the frames. Since the moving speed of probe 8 shown in FIG. 1 does not rapidly vary over a short interval, movement vector $\hat{S}_k$ of the $k^{th}$ frame is expressed by the following equation by taking into account correlation of a previous movement vector.

$$\hat{S}_k = \alpha S_k + (1-\alpha)\hat{S}_{k-1}, 0 \leq \alpha \leq 1 \quad \text{(Eq. 2)}$$

wherein $\hat{S}_{k-1}$ is the movement vector of the $(k-1)^{th}$ frame; $\alpha$ and $(1-\alpha)$ are weights; and $\alpha$ is defined to a range of $0 \leq \alpha \leq 1$ in order to obtain previous movement vectors and an average of the weights. Using the computed movement vector, plane location modifying unit 21 aligns a plurality of frames with no offset by estimating the movement between frames in the upper, lower, right, and left directions in 3D space.

Figure 6:
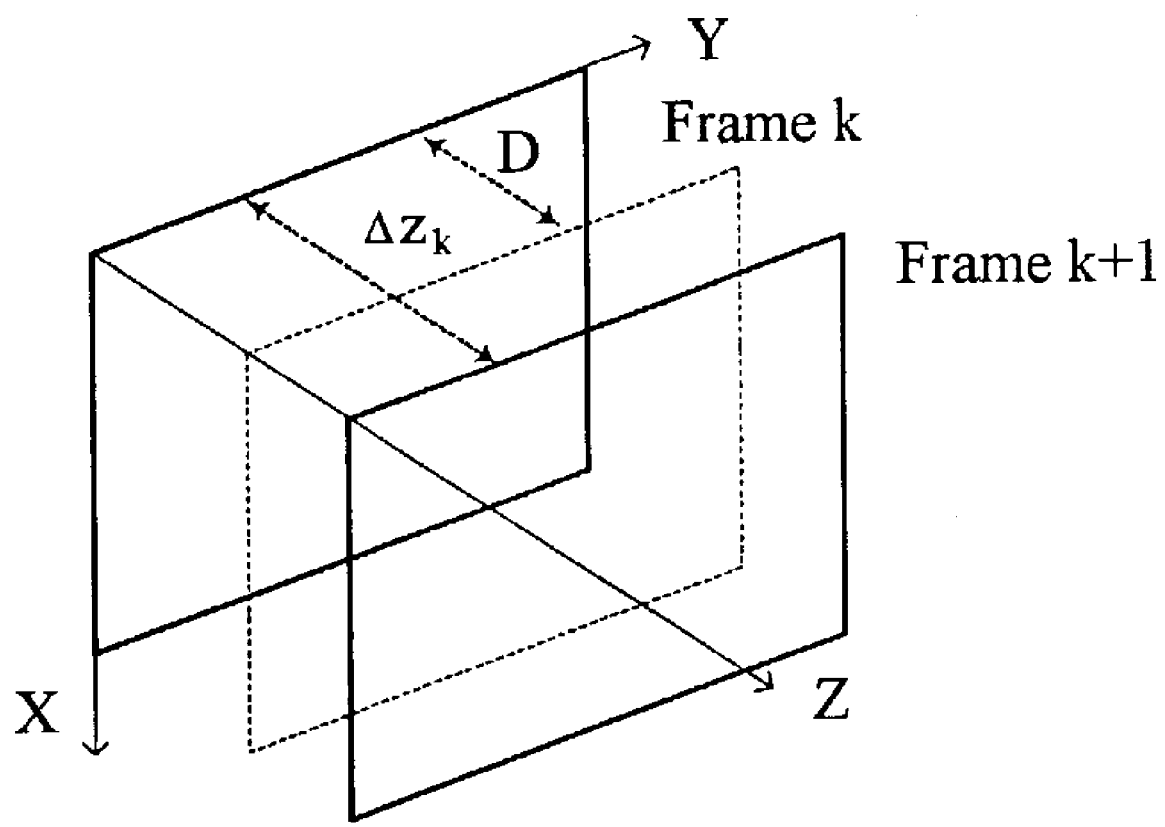
FIG. 6 illustrates the non-uniformity of the distances between frames.
Figure 7:
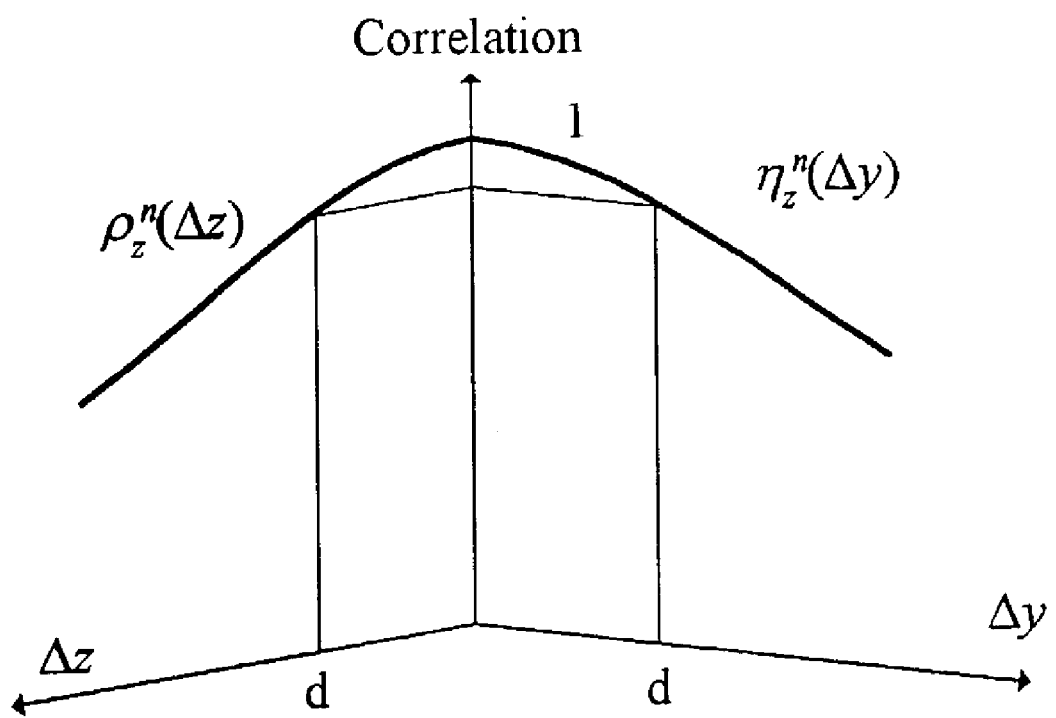
FIG. 7 is a partial isotropy with respect to a lateral distance correlation function and an elevation distance correlation function in the Y-Z plane.

Inter-frame distance estimating unit 22 estimates the distances between consecutive frames among the aligned frames and interpolates a location for each of the aligned frames to even the distances therebetween. Specifically, frame sequences inputted to inter-frame distance estimating unit 22 from plane location modifying unit 21 are aligned along the Z-axis as shown in FIG. 6. However, the distance between the frame sequences is not uniform. Referring to FIG. 6, which shows that the next frame, i.e., the $(k+1)^{th}$ frame, is obtained at a distance longer than uniform inter-frame distance D. Thus, in order to align frames at uniform inter-frame distance D, inter-frame distance estimating unit 22 assumes that a lateral distance correlation function between (x, y, z) and (x, y+$\Delta y$, z) is equal to an elevation distance correlation function between (x, y, z) and (x, y, z+$\Delta z$), within a short distance of $\Delta z = \Delta y$. Referring to FIG. 7, which shows a partial isotropy with respect to a lateral distance correlation function and an elevation distance correlation function in the Y-Z plane. The reason why make such assumption is such that tissue characteristics of minute parts of human organs may be same and image characteristics of the same are also same as they construct their images by using information received from a same ultrasound array with a same depth.

Inter-frame distance estimating unit 22 first divides frames into a plurality of blocks without overlapping each other and calculates a lateral distance correlation $\eta_z^n(d)$ per each block by using the following Equation 3. The lateral distance correlation means a correlation that is obtained on Y-axis in a lateral direction in a 3D space.

$$\eta_z^n(d) = \frac{\sum_{(x,y) \in B_n}[I_z(x,y) - \bar{I}_z^n][I_z(x, y+d) - \bar{I}_z^n(d)]}{\sqrt{\sum_{(x,y) \in B_n}[I_z(x,y) - \bar{I}_z^n]^2 \sum_{(x,y) \in B_n}[I_z(x, y+d) - \bar{I}_z^n(d)]^2}} \quad \text{(Eq. 3)}$$

wherein $\bar{I}_z^n(d)$ is an average brightness of a block moved by a distance d in Y-axis; $I_z(x, y)$ is a brightness at a coordinates (x, y, z) in a 3D space; and $B_n$ is an $n^{th}$ block within a frame.

Figure 8:
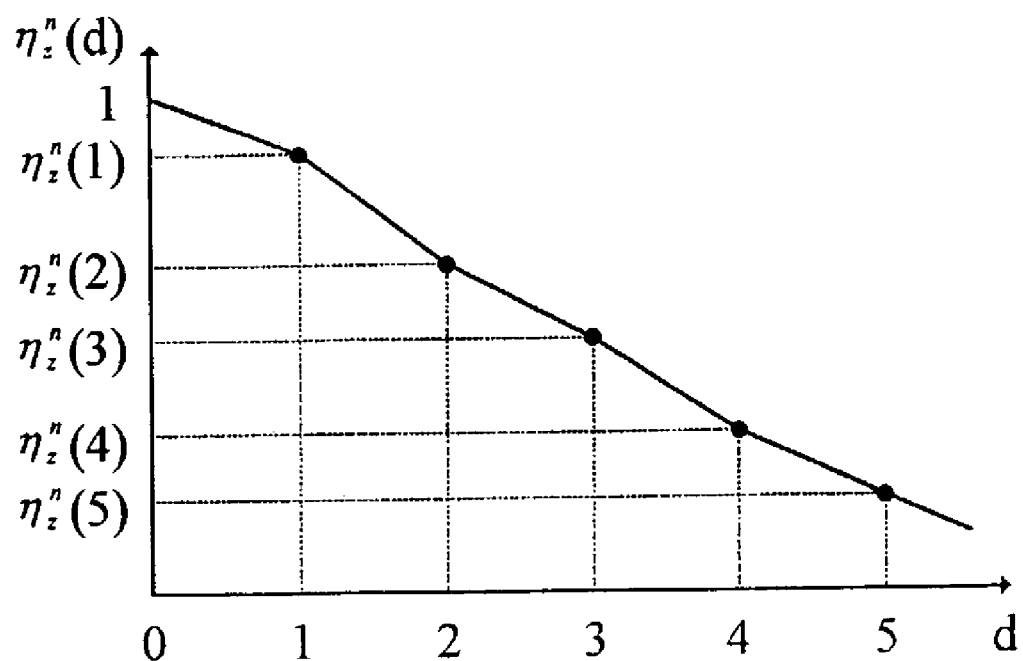
FIG. 8 is a graph showing a partial linear approximation of the lateral distance correlation function.

After calculating the lateral distance correlation $\eta_z^n(d)$, inter-frame distance estimating unit 22 performs a partial linear approximation on the calculated results as shown in FIG. 8. In FIG. 8, a horizontal axis represents the distance d between pixels and a vertical axis represents a correlation value. In the graph shown in FIG. 8, each point denoted by a symbol "●" indicates a value calculated by using Equation 3 on a pixel-by-pixel basis and correlation of each point is estimated by linearly drawing a line between points. The further the distance d from the starting point, the lower the correlation. Thus, the graph declines downwardly.

Thereafter, inter-frame distance estimating unit 22 calculates an elevation distance correlation $\rho_z^n$ by using Equation 4 as follows:

$$\rho_z^n = \frac{\sum_{(x,y) \in B_n}[I_z(x,y) - \bar{I}_z^n][I_{z+\Delta z}(x,y) - \bar{I}_{z+\Delta z}^n]}{\sqrt{\sum_{(x,y) \in B_n}[I_z(x,y) - \bar{I}_z^n]^2 \sum_{(x,y) \in B_n}[I_{z+\Delta z}(x,y) - \bar{I}_{z+\Delta z}^n]^2}} \quad \text{(Eq. 4)}$$

wherein $I_z(x, y)$ is a brightness of (x, y, z) in 3D space; $B_n$ is an $n^{th}$ block within a frame; $\bar{I}_z^n(d)$ is an average brightness of a block; $\Delta z$ is a distance between a frame located at a position z and the next frame; and $\rho_z^n$ is the elevation distance correlation obtained from each block.

Assuming the elevation distance correlation and the lateral distance correlation are partially isotropic, i.e., $\rho_z^n(\Delta z)$ $=\eta_z^n(\Delta y)$, with respect to the short distance of $\Delta z=\Delta y$, inter-frame distance estimating unit 22 estimates an $n^{th}$ distance $\Delta_z^n$ between blocks by using the following Equation 5 (FIG. 7 shows the assumption $\rho_z^n(\Delta z)=\eta_z^n(\Delta y)$ with respect to $\Delta z=\Delta y$).

$$\hat{\Delta}_z^n = \eta_z^{n-1}(\rho_z^n) \qquad \text{(Eq. 5)}$$

wherein the $n^{th}$ distance $\Delta_z^n$ is calculated by applying an $n^{th}$ block elevation distance correlation $\rho_z^n$ to an inverse function of an $n^{th}$ block lateral distance correlation $\eta_z^n$. Then, inter-frame distance estimating unit 22 estimates a distance $\Delta_z$ between consecutive 2D frames from the distance $\Delta_z^n$ by using Equation 6 as follows:

$$\hat{\Delta}_z = \frac{1}{|N_d|} \sum_{n \in N_d} \hat{\Delta}_z^n, \ N_d = \{n : |\hat{\Delta}_z^n - m| \langle \sigma \} \qquad \text{(Eq. 6)}$$

wherein m and $\sigma$ are an average and a standard deviation of $\Delta_z^n$ with respect to all blocks, respectively; and $|N_d|$ is a size of a set $N_d$.

Finally, inter-frame distance estimating unit 22 constructs consecutive frames with a uniform inter-frame distance shown in FIG. 9 by using a linear interpolation on the basis of the estimated inter-frame distances. The linear interpolation can be expressed as follows:

$$\hat{I}_{z_k+\delta}(x,y) = \frac{I_{z_{k+1}}(x,y) - I_{z_k}(x,y)}{\hat{\Delta}_{z_k}} \cdot \delta + I_{z_k}(x,y), \ 0 < \delta < \hat{\Delta}_{z_k} \qquad \text{(Eq. 7)}$$

wherein $\hat{I}$ is a new frame generated during the linear interpolation; $\delta$ is a predetermined value satisfying a relationship of $z_k+\delta=mD$ with respect to a positive integer m, where D is a desired uniform inter-frame distance; and $z_k$ is a coordinates value in an elevation axis of a $k^{th}$ frame.

As described above, plane location modifying unit 21 aligns a plurality of consecutive frames with no offset in 3D space and inter-frame distance estimating unit 22 estimates a distance between two frames among the aligned consecutive frames and interpolates a location of each frame to make the distance uniform. Therefore, 2D ultrasound frame sequences inputted to 2D/3D converter 16 are constructed as a 3D image having a minimum image distortion.

In addition, a rotation angle of a present frame with respect to a previous frame on the X-Y-Z axis can be computed as follows. First, the present frame is divided into a plurality of blocks and a rotation angle of each block is calculated by using the following Equation 8 defined by:

$$(\alpha_n, \beta_n, \gamma_n) = \underset{\alpha, \beta, \gamma}{\text{argmin}} D[B'_n(\alpha, \beta, \gamma), B_n] \qquad \text{(Eq. 8)}$$

wherein $B_n$ is an $n^{th}$ block of a present frame; $B'_n(\alpha, \beta, \gamma)$ is a block of which an $n^{th}$ block of a previous frame is rotated by $(\alpha, \beta, \gamma)$; and $D[B'_n(\alpha, \beta, \gamma), B_n]$ is an error between the $n^{th}$ blocks of the present and previous frames. An angle that produces the smallest error is selected as the rotation angle of each block. By averaging the rotation angles of the blocks in the present frame, the rotation angle of the present frame is obtained.

If a present frame has been rotated by $(\alpha, \beta, \gamma)$, an error which occurred, is eliminated through the rotation of the present frame by $(-\alpha, -\beta, -\gamma)$. Coordinates (x', y', z') for a frame having a corrected rotation error is calculated from coordinates (x, y, z) within a frame having a rotation error, by using the following Equation 9 defined by:

$$\begin{bmatrix} x' \\ y' \\ z' \end{bmatrix} = R_z R_y R_x \begin{bmatrix} x \\ y \\ z \end{bmatrix} \qquad \text{(Eq. 9)}$$

$$R_z = \begin{pmatrix} \cos\gamma & \sin\gamma & 0 \\ -\sin\gamma & \cos\gamma & 0 \\ 0 & 0 & 1 \end{pmatrix}, R_y = \begin{pmatrix} \cos\beta & 0 & -\sin\beta \\ 0 & 1 & 0 \\ \sin\beta & 0 & \cos\beta \end{pmatrix},$$

$$R_x = \begin{pmatrix} 1 & 0 & 0 \\ 0 & \cos\alpha & \sin\alpha \\ 0 & -\sin\alpha & \cos\alpha \end{pmatrix}$$

As described above, the 3D ultrasound imaging method and apparatus in accordance with the present invention is capable of accurate estimation of a distance between consecutive 2D frames obtained by a manual scanning method, which does not require any conventional mechanical devices or location detection sensors, thereby minimizing image distortions caused during the generation of a 3D ultrasound image. Thus, the reliability of measured 3D ultrasound images is improved.

Further, the 3D ultrasound imaging apparatus in accordance with the present invention employs a manual scanning method, which can resolve inconveniences in actual use of those conventional mechanical devices and remarkably lower the manufacturing cost of an ultrasound imaging apparatus.

While the present invention has been shown and described with respect to the particular embodiments, those skilled in the art will recognize that many changes and modifications may be made without departing from the spirit and scope of the invention as defined in the appended claims.

What is claimed is:

1. A three-dimensional ultrasound imaging apparatus, comprising:
   a transducer array for transmitting ultrasound signals to a target object and receiving echo signals reflected from the target object, wherein the transducer array is comprised of a plurality of transducer elements;
   means for receive-focusing the echo signals from the transducer array to generate a plurality of consecutive two-dimensional ultrasound image frames;
   means for converting the consecutive two-dimensional ultrasound image frames into a three-dimensional ultrasound image, wherein the converting means comprises:
   a plane location modifying unit for aligning the consecutive two-dimensional ultrasound image frames with no offset to each other in a three-dimensional space by estimating an inter-frame movement in upper, lower, right and left directions; and
   an inter-frame distance estimating unit for estimating a distance between two adjacent frames among the aligned two-dimensional ultrasound image frames and interpolating a frame location of the respective aligned two-dimensional image frames as a lateral distance correlation function obtained in a lateral direction on a plane defined by the lateral direction and an elevation direction of the two-dimensional ultrasound image frames in a three-dimensional space, wherein the lateral distance correlation function is partially isotropic with an elevation distance correlation function obtained in the elevation direction, to thereby make an inter-frame distance uniform; and a display for displaying the three-dimensional ultrasound image.

2. The apparatus of claim 1, wherein the receive-focusing means further comprises:
   a pre-amplifier for amplifying the echo signals from the transducer array into a predetermined signal level;
   a time-gain-compensation (TGC) amplifier for varying a gain of the amplified signals from the pre-amplifier with respect to time and amplifying the gain-varied signals to compensate for attenuation of the gain-varied signals due to a ultrasound receiving distance;
   a beamformer for performing a receive-focusing on the compensated signals from the TGC amplifier in a lateral direction; and
   an analog-to-digital (A/D) converter for converting the receive-focused signals from the beamformer from analog to digital.

3. The apparatus of claim 1, wherein the image converting means further comprises:
   a three-dimensional volume constructing unit for obtaining three-dimensional volume information from the aligned consecutive two-dimensional image frames; and
   a rendering unit for constructing the three-dimensional image through a rendering process.

4. The apparatus of claim 1, wherein the plane location modifying unit divides each of the aligned two-dimensional ultrasound image frames into a plurality of blocks and obtains vectors for the blocks to calculate a movement vector for each frame by using a vector having a high frequency among the vectors for the blocks.

5. The apparatus of claim 4, wherein the movement vector for each frame is calculated based on a block matching that is executed up to half pixels in each block, each half pixel is a potential pixel lying halfway between two pixels and its intensity is estimated through a bilinear interpolation.

6. The apparatus of claim 1, wherein the inter-frame distance estimating unit divides each of the aligned two-dimensional ultrasound image frames into a plurality of blocks and estimates distances per each block to estimate a distance between the two adjacent frames by using an average distance of the estimated distances.

7. A three-dimensional ultrasound imaging method, comprising the steps of:
   a) transmitting ultrasound signals to a target object and receiving echo signals reflected from the target object;
   b) receive-focusing the echo signals to generate a plurality of consecutive two-dimensional ultrasound image frames;
   c) converting the consecutive two-dimensional ultrasound image frames into a three-dimensional ultrasound image, wherein the step c) includes the steps of:
      c1) aligning the consecutive two-dimensional ultrasound image frames with no offset to each other in a three-dimensional space by estimating an inter-frame movement in upper, lower, right and left directions; and
      c2) estimating a distance between two adjacent frames among the aligned two-dimensional ultrasound image frames and interpolating a frame location of the respective aligned two-dimensional image frames as a lateral distance obtained in a lateral direction on a plane defined by the lateral direction and an elevation direction of two-dimensional ultrasound image frames in a three-dimensional space, wherein the lateral distance is partially isotropic with an elevation distance correlation function obtained in the elevation direction; and
   d) displaying the three-dimensional ultrasound image.

8. The method of claim 7, wherein the step c1) further comprises the steps of dividing each of the aligned two-dimensional ultrasound image frames into a plurality of blocks and obtaining vectors for the blocks to calculate a movement vector for each frame by using a vector having a high frequency among the vectors for the blocks.

9. The method of claim 7, wherein the step c2) further comprises the steps of dividing each of the aligned two-dimensional ultrasound image frames into a plurality of blocks and estimating distances per each block to estimate a distance between the two adjacent frames by using an average distance of the estimated distances.

* * * * *